United States Patent
Michalke et al.

(10) Patent No.: US 10,306,821 B2
(45) Date of Patent: Jun. 4, 2019

(54) DEVICE AND METHOD FOR CONTROLLING THE OPERATION OF A TOWED IMPLEMENT, WHICH CAN BE ACTIVATED HYDRAULICALLY, ON A VEHICLE

(71) Applicant: Robert Bosch GmbH, Stuttgart (DE)

(72) Inventors: Gabriele Michalke, Weil der Stadt (DE); Markus Schleyer, Ludwigsburg (DE); Steffen Rose, Ludwigsburg (DE); Tillmann Falck, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 118 days.

(21) Appl. No.: 15/373,530

(22) Filed: Dec. 9, 2016

(65) Prior Publication Data

US 2017/0164549 A1    Jun. 15, 2017

(30) Foreign Application Priority Data

Dec. 10, 2015 (DE) .......................... 10 2015 224 757

(51) Int. Cl.
*A01B 63/111* (2006.01)
*A01B 63/10* (2006.01)
(Continued)

(52) U.S. Cl.
CPC ............ *A01B 63/111* (2013.01); *A01B 63/10* (2013.01); *A01B 63/1013* (2013.01);
(Continued)

(58) Field of Classification Search
CPC ... B64F 1/22; B64F 1/227; B64F 1/10; G01N 3/08; G01N 23/04; G01V 5/0008; B60K 28/00; B60P 1/00; B60P 3/00; B60P 3/32; G06F 11/30; G06F 3/0488; G06F 3/017; E02D 5/80; G01M 5/005; B62D 49/00;
(Continued)

(56) References Cited

U.S. PATENT DOCUMENTS 6,663,132 B1 * 12/2003 Kizy .................. B60D 1/26
                                            280/479.1
2007/0166138 A1 * 7/2007 Brooks ............... A01D 87/122
                                            414/471

(Continued)

FOREIGN PATENT DOCUMENTS

DE    10 2011 079 632 A1    1/2013
EP         1 238 577 A1     9/2002
(Continued)

*Primary Examiner* — Behrang Badii
(74) *Attorney, Agent, or Firm* — Maginot, Moore & Beck LLP

(57) ABSTRACT

The disclosure relates to a device of a vehicle, in particular a tractor, having a hydraulic activation unit for controlling the operation of a towed implement on the vehicle, comprising at least one position detection unit with at least one camera, position detection marks, and an evaluation unit and a data-transmitting connection to a control unit which is assigned to the hydraulic activation unit. Furthermore, a method is proposed, wherein by means of such a position detection unit the position of the towed implement can be determined, and the position can be adjusted according to requirements by suitable operation of the hydraulic activation unit.

6 Claims, 2 Drawing Sheets

(51) Int. Cl.
*A01B 76/00* (2006.01)
*A01B 69/00* (2006.01)
*A01B 71/02* (2006.01)
*B60D 1/36* (2006.01)
*B60K 28/00* (2006.01)
*B64F 1/22* (2006.01)
*G01B 21/06* (2006.01)
*B62D 49/00* (2006.01)
*G01N 3/08* (2006.01)
*A01D 87/12* (2006.01)
*B60D 1/00* (2006.01)
*B62D 13/06* (2006.01)
*B60P 1/04* (2006.01)
*E02D 5/80* (2006.01)
*B66F 9/08* (2006.01)

(52) U.S. Cl.
CPC ............ *A01B 69/001* (2013.01); *A01B 71/02* (2013.01); *A01B 76/00* (2013.01); *A01D 87/122* (2013.01); *B60D 1/00* (2013.01); *B60D 1/36* (2013.01); *B60K 28/00* (2013.01); *B60P 1/04* (2013.01); *B62D 13/06* (2013.01); *B62D 49/00* (2013.01); *B64F 1/22* (2013.01); *B64F 1/227* (2013.01); *B66F 9/082* (2013.01); *E02D 5/80* (2013.01); *G01B 21/06* (2013.01); *G01N 3/08* (2013.01)

(58) Field of Classification Search
CPC ....... B62D 13/06; B62D 15/027; B60S 13/02; E01F 13/022; E01F 15/00; F41H 11/13; F41H 11/12; F41H 5/24; F41H 13/00; F41H 5/20; F41H 5/18; F41H 11/00; G01B 21/06; B60D 1/36; B60D 1/245; B60D 1/62; F21S 45/48; F21S 41/143; F21S 41/28; F21S 45/00; B60Q 1/22; B60Q 1/2634; B60Q 1/2661; B60Q 1/305; B60Q 5/005; A01B 63/111; A01B 63/10; A01B 63/1013; A01B 69/001; A01B 71/02; A01B 76/00; B60W 30/00; H04N 7/18; H04N 7/183; G06K 9/00355

See application file for complete search history.

(56) References Cited

U.S. PATENT DOCUMENTS

| | | | |
|---|---|---|---|
| 2009/0198425 A1 | 8/2009 | Englert | |
| 2011/0224845 A1* | 9/2011 | Perry | B64F 1/22 |
| | | | 701/2 |
| 2012/0185131 A1 | 7/2012 | Headley | |
| 2013/0098165 A1* | 4/2013 | Bruce | G01N 3/08 |
| | | | 73/828 |
| 2014/0210456 A1* | 7/2014 | Crossman | B62D 13/06 |
| | | | 324/207.2 |
| 2014/0267688 A1* | 9/2014 | Aich | H04N 7/181 |
| | | | 348/113 |
| 2014/0297128 A1* | 10/2014 | Lavoie | G01B 21/06 |
| | | | 701/41 |
| 2015/0077557 A1 | 3/2015 | Han et al. | |

FOREIGN PATENT DOCUMENTS

| | | |
|---|---|---|
| EP | 1 862 050 A2 | 12/2007 |
| WO | 2012/103193 A1 | 8/2012 |

* cited by examiner

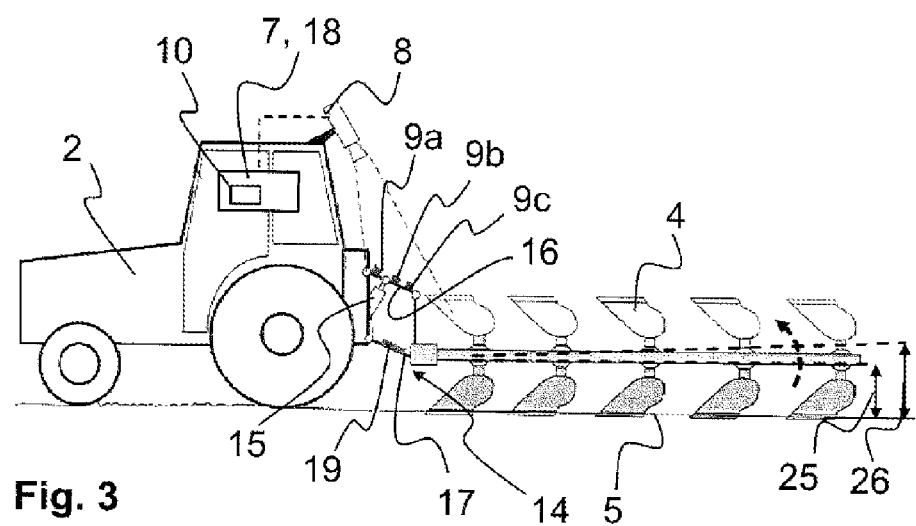
Fig. 3
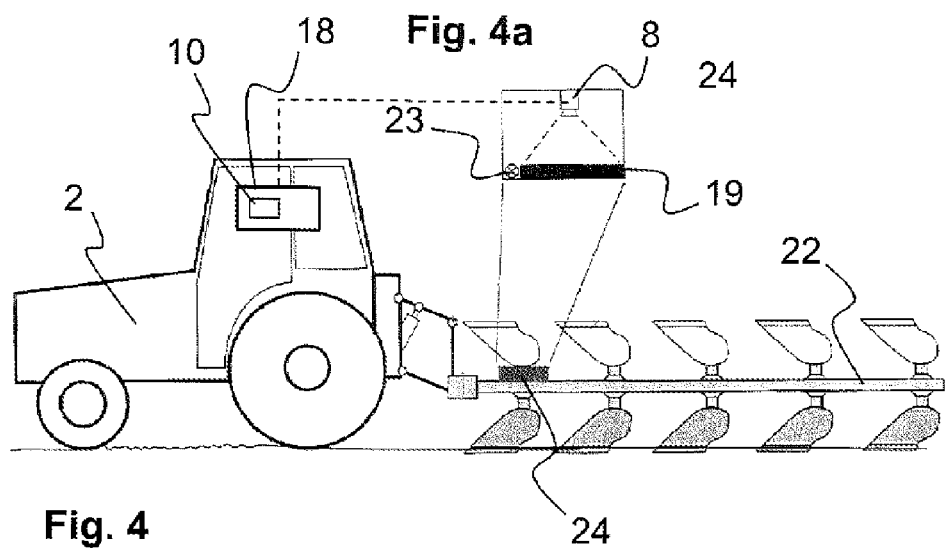
Fig. 4
Fig. 4a

DEVICE AND METHOD FOR CONTROLLING THE OPERATION OF A TOWED IMPLEMENT, WHICH CAN BE ACTIVATED HYDRAULICALLY, ON A VEHICLE

This application claims priority under 35 U.S.C. § 119 to application no. DE 10 2015 224 757.0, filed on Dec. 10, 2015 in Germany, the disclosure of which is incorporated herein by reference in its entirety.

BACKGROUND

The present disclosure relates to a device for a vehicle, in particular a tractor, having a hydraulic activation unit for controlling the operation of a towed implement on the vehicle, and to an operating method which is suitable for said device.

SUMMARY

In particular, the disclosure is applied in a tractor, an agricultural tractor, a mobile working machine for working fields or the like. Tractors or agricultural tractors are used predominantly in agriculture as universally employable working machines for working arable land. Plowing, as one of the most frequent applications, makes high demands on the drive train of the tractor and of the control quality of an electronic-hydraulic lifting mechanism control system because plowing work can be carried out quickly and efficiently only with coordinated operation. In particular in the case of highly non-homogeneous and very wet ground there is the possibility that a very large resistance force at the plow will cause the tractor to become stuck and/or the engine to stall. In addition to positional control of the plow, a tensile force control system can be provided which attempts to prevent the engine from stalling by measuring the tensile force at the tractor-side joint of the lower link and said force or its gradient is then adjusted to a value which prevents stalling of the engine or brings about a reduction in the slip of the drive wheels. This is done, in particular, through (briefly) raising the plow and through the resulting reduction in the resistance force acting on the plow. In addition, in the case of very non-homogeneous ground the result of the plowing process is improved, since the plow would reduce its plowing depth in very dense soil regions. In the case of very undulating and uneven ground, the plowing pattern is also improved and the comfort increased, since the plowing depth is better adapted to the profile of the ground by means of the varying tensile force than if the plow were to be controlled with respect to the position or depth thereof.

In order to control the position of the plow it is known to use the position of the lifting mechanism as a control variable. The position sensor, which is activated by a cam plate in the lifting mechanism, supplies the actual value. A tensile force control circuit which is additionally superimposed on the position control system provides two force measuring pins for determining the tensile force, said pins being installed in the joint of the lower link.

Even if the described approaches for operating such tractors or agricultural tractors already supply good results, the available systems are nevertheless to a certain extent too complex and therefore too cost-intensive and also insufficiently reliable and/or too inaccurate. In this regard, there is a need for improvements in particular in respect of the determination of the position of the towed implement or the determination of the tensile force.

Taking this as a basis, the object of the present disclosure is to provide a device and a method which mitigate the abovementioned disadvantages or even avoid them. In particular, the determination of the position of the towed implement and of the tensile force are to be improved in a structurally simple way which is suitable for the ambient conditions in the field.

These objects are achieved with a device and a method according to the disclosure. Further refinements of the disclosure are specified in the disclosed embodiments. It is to be noted that the description, in particular with respect to the figures, introduces further details and developments of the disclosure which can be combined.

A contribution is made to this by a device on a vehicle having a hydraulic activation unit for controlling the operation of a towed implement on the vehicle, comprising at least one position detection unit with at least one camera, at least one position detection mark, an evaluation unit and a data-transmitting connection to a control unit which is assigned to the hydraulic activation unit.

The vehicle is, in particular, a tractor or what is referred to as an agricultural tractor. The towed implement is considered to be, in particular, a plow or a similar soil-working implement. In order to determine the position, in particular the vertical position of the towed implement above the ground, a position detection unit is provided which comprises at least one camera and one or more position detection marks. A position detection mark can be a visually conspicuous element, wherein this may be two-dimensional (e.g. in a manner of dashes, symbols, labels) and/or three-dimensional (e.g. in the manner of nipples, flags etc.). The position detection mark is preferably "passive", but it can also be provided e.g. with separate lighting means. Preferably at least two, in particular at least three position detection marks (spaced apart from one another) are provided, which position detection marks can, in particular, all be detected by a fixed (possibly also movable) camera. An associated evaluation unit is connected to the at least one camera electrically and in a data-transmitting fashion and is designed to control the operation thereof and to process the measurement signals thereof. The evaluation unit is configured, in particular, to perform analysis of the image data of the camera, with the result that the position detection marks can be detected or determined unambiguously with respect to their position.

The position determined in the evaluation unit can be compared with, or influenced by, parameters which have been predefined (e.g. stored and/or set by the operator of the vehicle), wherein a control signal is then also transmitted to the control unit, and in the process the operation of the hydraulic activation unit of the towed implement can be influenced. The evaluation unit can be a separate (electronic) assembly, but it is also possible for the evaluation unit to be part of the actual control unit for actuating the hydraulic activation unit. The (at least one) data-transmitting connection between the evaluation unit and the control unit can be implemented in a cable-bound or cableless fashion. The control unit and/or the evaluation unit can be assigned to a vehicle controller or configured independently thereof.

The at least one camera is expediently directed toward the at least one position detection mark for this purpose. This can be the case permanently, or else the setting can also be made according to requirements (temporarily).

The at least one position detection mark is arranged at least on the towed implement or on a (vehicle-side) lifting mechanism of the towed implement. If a plurality of position detection marks are provided, they can also be positioned both on the towed implement as well as on the lifting mechanism.

The embodiment in which the at least one camera is directed toward the towed implement and the position detection marks are positioned on the towed implement, provides the advantage that the known geometry or the dimensions of a specific plow are stored in the evaluation unit, the control unit or the vehicle controller and can therefore be made available easily for the evaluation. Therefore, under certain circumstances the accuracy of the evaluation can be improved with respect to specifically stored shapes of the towed implement.

The further preferred embodiment according to which the camera is directed toward the (vehicle-side) lifting mechanism and the position detection marks are positioned e.g. on an upper link of the lifting mechanism has the advantage that it is independent in the current type of the towed implement, with the result that an exchange of different towed implements is easily possible without reconfiguring for this purpose the subsequent method explained in detail and/or the towed implement itself.

It is expedient for this that the at least one camera is arranged on the vehicle and/or the towed implement. If appropriate, a plurality of cameras can also be provided, with the result that the vehicle and the towed implement can be embodied with a camera to which specific functions (determination of position and/or tensile force) are assigned.

In addition to the position detection device, a tensile force-measuring apparatus is advantageously present, which is connected in a data-transmitting fashion to the evaluation unit. The tensile force-measuring apparatus is preferably coupled to the at least one camera which is directed toward a stress-optical material.

The term "stress-optical material" is understood here to refer, in particular, to a material which changes its form, e.g. its shape and/or color, owing to different stress states. Under certain circumstances it is possible for the stress-optical material to have and/or form a surface mark which is changed in reaction to changed force effects. For this purpose, in particular a material from the following group is proposed: Plexiglas, Araldite (epoxy resin), Makrolan.

In the stress optics which are used here, in particular materials (or components) made of special transparent plastics are irradiated with polarized light while being mechanically loaded. The stress state in the material then changes the polarization of the light. Depending on the local stress state and the precise arrangement at an object, for example bright, dark and/or colored strips (isoclines and isochromats) appear on the material when the material is considered through a polarization filter which is a component of a camera or can interact therewith. The stress distribution in the material can be inferred from this strip pattern. Reference-strip patterns for various tensile force situations can be made available for this and compared with the strip pattern detected by the camera at that particular time. Consequently, the currently prevailing tensile force at the towed implement can be determined or estimated from this.

The stress-optical material is expediently attached to the towed implement and/or to the lifting mechanism. If expedient, the strip-optical material is attached to the towed implement, in particular fastened directly to the trailer of the plow, with the result that stresses prevailing can be detected directly on the towed implement. In the event of the stress-optical material being positioned on the lower link of the lifting mechanism, the transmission of energy and data to the vehicle can be carried out over a particularly short path, by which means a compact and simple arrangement which is resistant to interference is implemented.

If desired, the tensile force measurement device which is proposed here can be applied independently of the position detection unit, e.g. with the following design: device on a vehicle having a hydraulic activation unit for controlling the operation of a towed implement on the vehicle, comprising at least one tensile force-measuring apparatus with at least one camera, at least one stress-optical material, an evaluation unit and a data-transmitting connection to a control unit which is assigned to the hydraulic activation unit. In so far as developments relating to the tensile force-measuring apparatus are disclosed here they can equally well apply to this device.

The hydraulic activation unit preferably comprises a lifting mechanism for the towed implement, which lifting mechanism can be actuated by the evaluation unit. In particular electrical or data-transmitting connections are provided for this. In particular, the evaluation unit and the lifting mechanism are configured in such a way that the evaluation unit can set at least one state variable and/or can access an actuation element of the lifting mechanism.

Further details of the device can be found in the following explanation of the operating methods. In particular, the explanations relating to the methods can be used here in a supplementary fashion. The above explanations relating to the device can also be used to supplement the description of the methods.

According to a further aspect, a method for operating a vehicle, in particular a tractor, with a hydraulic activation unit for controlling the operation of a towed implement on the vehicle is proposed. The method in this case is carried out with the device likewise proposed herein, the evaluation unit in particular being configured to carry out the method. The method comprises at least the following steps:
a) detecting the at least one position detection mark by means of a camera directed toward the latter;
b) determining a vertical position of the towed implement with respect to the ground from the detected position of the position detection marks and the known shape of the towed implement;
c) comparing the determined vertical position with a reference vertical position;
d) activating the hydraulic activation unit if the determined vertical position differs from a reference vertical position.

Steps a) to d) are preferably carried out in the specified sequence, wherein the steps can nevertheless be repeated at least partially with a chronological overlap and/or separately. Therefore, it may be the case, for example, that the steps a) to c) are repeated more frequently before step d) is carried out, specifically, in particular, once the condition in step d) is met.

In order to carry out step a), a selected camera, or one which is possibly specially configured, detects the at least one position detection mark, wherein said camera can create, in particular, an image thereof and can transfer it to the evaluation unit. For this purpose, the camera can be moved or pivoted and/or secured in a positionally fixed fashion in one position. This image can be analyzed simultaneously and/or buffered if appropriate.

On the basis of this (image) data which is generated by the camera it is possible, according to step b), to determine at least the vertical position of the towed implement with respect to the ground from the detected position of the position detection marks and the known shape of the towed implement. The (in particular geodetic) "vertical position"

relates in this context preferably to a characteristic variable which represents, for example, a statement about the penetration depth of the towed implement into the ground.

The vertical position which is determined in this way can be compared, in particular, with a reference vertical position in the evaluation unit (step c)). The reference vertical position can be stored or saved in the vehicle and made available to the evaluation unit. The (current) reference vertical position is selected, in particular, as a function of at least one (current) operating parameter of the vehicle (e.g. velocity, engine load etc.) and/or the hydraulic activation unit (e.g. lifting mechanism position etc.). In this respect, it is checked, in particular, whether a desired or expected reference vertical position is actually present at the time.

According to step d), if the determined vertical position differs from the current relevant or expected reference vertical position, the hydraulic activation unit is activated in order to adapt the current position of the towed implement to the reference vertical position, that is to say, in particular, to raise or lower the vertical position of the towed implement above the ground. Optionally, this activation process can also be monitored and controlled with the steps specified in steps a) to c). However, it is also possible for a separate specification to be permanently predefined from the comparison according to step c) and controlled.

It is preferred that all the steps a) to d) are carried out while the vehicle is travelling. It is quite particularly preferred for the method to be initiated by the driver and/or automatically with predefinable driving situations and then carried out intermittently and/or continuously until it is ended by the driver and/or automatically in a predefinable driving situation.

According to a further aspect, a further method for operating a vehicle having a hydraulic activation unit for controlling the operation of a towed implement on the vehicle is proposed. The method in this case is carried out with the device likewise proposed herein with a tensile force-measuring apparatus, the evaluation unit in particular being configured to carry out the method. The method comprises at least the following steps:
A) detecting the state of the stress-optical material by means of a camera which is directed toward the latter;
B) determining a tensile force on the towed implement from the detected state of the stress-optical material;
C) comparing the determined tensile force with a reference tensile force;
D) activating the hydraulic activation unit if the determined tensile force differs from a reference tensile force.

The steps A) to D) are preferably carried out in the specified sequence, although the steps can at least partially be repeated with a chronological overlap and/or separately. It is therefore possible, for example, for the steps A) to C) to be repeated more frequently before step D) is carried out, specifically, in particular, once the condition in step D) is met.

In order to carry out step A), a selected camera, or possibly one which is specially configured, detects the state of the stress-optical material, wherein it creates, in particular, an image thereof and can transmit it to the evaluation unit. For this purpose, the camera can be moved or pivoted and/or be secured in a positionally fixed fashion in one position. This image can be simultaneously analyzed and/or, if appropriate, buffered. For this purpose, the camera can also be equipped with a polarization filter or interact with such a filter.

Taking this (image) data generated by the camera as a basis, according to step B) at least the tensile force at the towed implement can be determined. The tensile force means here, in particular, the characteristic value from the force which has to be applied by the vehicle in order to tow the towed implement. The tensile force is in particular also dependent on the penetration depth of the towed implement into the ground.

The tensile force which is determined in this way can be compared with a reference tensile force, in particular in an associated evaluation unit (step C)). The reference tensile force can be stored or saved in the vehicle and made available to the evaluation unit. The (current) reference tensile force is selected, in particular, as a function of at least one (current) operating parameter of the vehicle (e.g. speed, engine load, etc.) and/or the hydraulic activation unit (e.g. lifting mechanism position etc.). In this respect, it is checked in particular whether a desired or expected reference tensile force is actually present at that time.

According to step D) when the determined tensile force differs from the current relevant or expected reference tensile force the hydraulic activation unit is activated in order to adapt the current position of the towed implement in such a way that the reference tensile force is reached better, that is to say in particular the vertical position of the towed implement above the ground is raised or lowered. If appropriate, this activation process can also be monitored and controlled with the steps specified in steps A) to C). However, it is also possible for a separate specification to be permanently predefined from the comparison according to step C) and controlled.

It is preferred that all the steps A) to D) are carried out while the vehicle is travelling. It is quite particularly preferred for the method to be initiated by the driver and/or automatically with predefinable driving situations and then carried out intermittently and/or continuously until it is ended by the driver and/or automatically in a predefinable driving situation.

The tensile force is preferably additionally determined with a tensile force-measuring apparatus. The tensile force which is determined by means of the tensile force-measuring device is advantageously used if a predefined difference parameter is reached by an expected tensile force. The expected tensile force is preferably made available by the operator of the vehicle.

The arrangement and/or method presented here for position control provide, in particular, the following advantages, in that by measuring the position by means of the camera and the position detection marks the position or depth of the implement, in particular of a plow, can be brought about in a reliable, precise and technically simple fashion.

BRIEF DESCRIPTION OF THE DRAWINGS

The disclosure and the technical field are explained in more detail below with reference to figures. Here, identical components are characterized with the same reference signs. The illustrations are schematic and not provided for the illustration of size ratios. The explanations which are given with respect to individual details of the figure can be extracted and are freely combinable with contents from other figures or the description above, unless something else necessarily arises for a person skilled in the art or such a combination is explicitly prohibited here.

In the drawings:

FIG. 3 shows a side view according to FIG. 1 in which the camera is directed towards the lifting mechanism, and on the lifting mechanism the position detection marks are positioned on the upper link, and the stress-optical material is positioned on the lower link;

FIG. 4 shows a side view according to FIG. 1 in which the position detection unit is positioned with an integrated camera on the towed implement; and FIG. 4a shows a detail of the position detection unit with an integrated camera.

DETAILED DESCRIPTION

Figure 1:
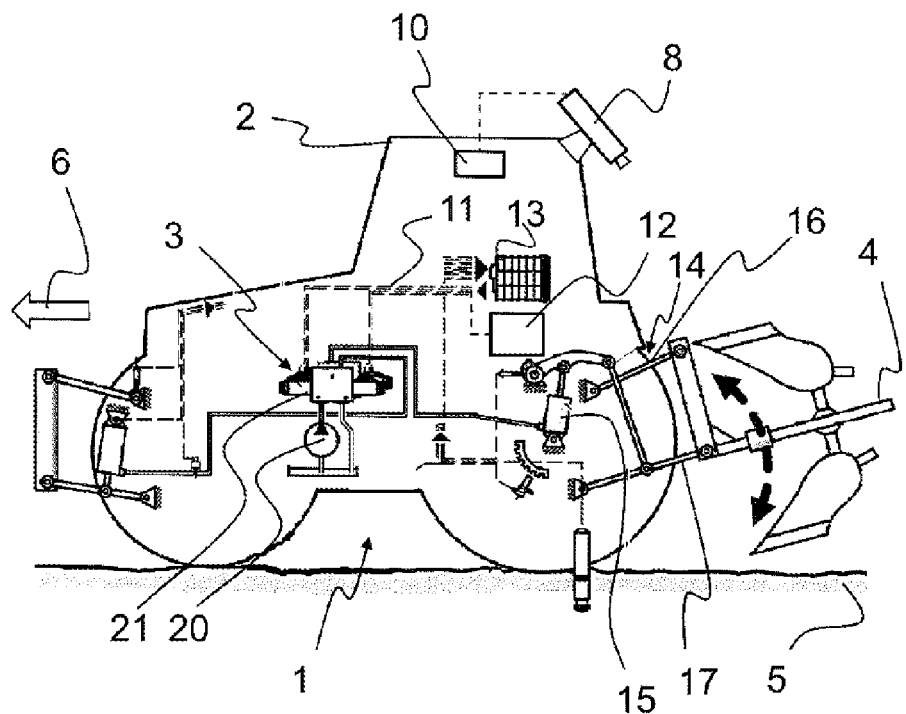
FIG. 1 shows a schematic side view of a tractor with a hydraulic activation unit for controlling the operation of a towed implement comprising a camera for a position detection unit.

FIG. 1 shows the basic illustration of the device 1 specified here on a vehicle 2, in particular of the type of a tractor during working of the soil with a towed implement 4, in particular with a plow. Here, the vehicle 2 tows the towed implement 4 behind it while driving in the driving direction 6 and through an upper layer of the ground. The general driving mode of the vehicle 2 can be influenced by means of a (if appropriate separate) vehicle controller 12. The position of the towed implement 4 can be set with a hydraulic activation unit 3 having a control unit 13 for actuating the hydraulic activation unit 3 and a lifting mechanism 15. The hydraulic activation unit 3 can be constructed, in particular, as follows: the pump 20 delivers a flow of oil to the regulating valve 21 which controls the lifting mechanism 15. Said lifting mechanism acts on the lower links 17, as a result of which the towed implement 4 can be raised, held in position or lowered.

Furthermore, a camera 8 of a position detection unit 7 is provided which is attached to or on the vehicle 2. The camera 8 is directed towards the towed implement 4 (illustrated in a cut-away view and forming a plow here). The camera 8 can be e.g. a reversing camera which is suitable for optical measurements or a digital camera (high-resolution) which is installed specifically for the application purpose described here, and preferably with a polarization filter.

Figure 2:
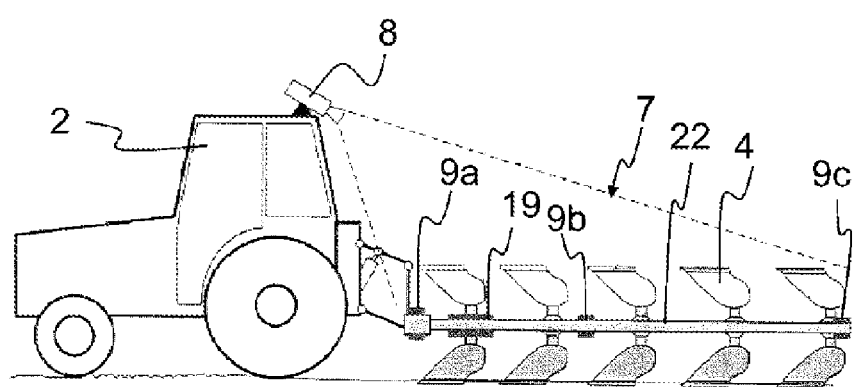
FIG. 2 shows a side view according to FIG. 1 in which the camera mounted on the vehicle is directed towards the towed implement and position detection marks of the position detection unit and a stress-optical material of a tensile force-measuring apparatus are positioned on the towed implement.

In order to be able to determine the position of the plow in space and therefore also its depth or height (vertical position 25), according to FIG. 2 three visually salient position detection marks 9a, 9b and 9c are provided on each side of the plow. In addition, the geometry or the dimensions of the plow are known. In order to determine a tensile-force-equivalent value for the tensile force controller, a stress-optical material 19, suitable for stress-optical recordings, is fastened to the carrier 22 of the plow at the level of the first pair of blades, e.g. by means of adhesive. Owing to the deformation which is dependent on the tensile force during plowing and is caused by tensile stresses or bending stresses in the carrier 22, an equivalent of the tensile force is inferred through evaluation of the camera images.

According to FIG. 3, the position detection marks 9a, 9b and 9c for determining the position or inclination of the lifting mechanism 14 are provided directly on the upper link 16 of the (vehicle-side) lifting mechanism 14. In addition, the stress-optical material 19 is fastened to the lower link 17 of the lifting mechanism 14. The arrangement has the advantage that it is independent of the selection of the towed implement 4. Therefore, the towed implements 4 do not have to be equipped with these position detection marks and/or stress-optical materials, and it is substantially easier to exchange the towed implements 4.

In addition, in both variants according to FIGS. 2 and 3 light sources (not illustrated here explicitly) can be provided in the region of the stress-optical material 19 if the ambient light is not sufficient for visual evaluation. At least one optical position detection mark 9a, 9b, 9c can basically be embodied e.g. also as infrared LEDs. This permits use of the measurement principle even in the case of low ambient lighting (e.g. at night).

In addition, by way of example a method for operating the vehicle 2 with a hydraulic activation unit for controlling the operation of a towed implement 4 is illustrated here. Firstly, the position detection marks 9a, 9b, 9c are detected by means of the camera 8 directed towards them. Then, the (current) vertical position 25 of the towed implement 4 is determined with respect to the ground 5 from the detected position of the position detection marks 9a, 9b, 9c and the known shape of the towed implement 4. The vertical position 25 which is determined in this way is then compared with a (stored or desired) reference vertical position 26. If the determined vertical position 25 differs from a reference vertical position 26 (more than desired or permitted), the hydraulic activation unit or the lifting mechanism 15 is activated and the towed mechanism 4 is pivoted.

FIG. 4 shows the combination of the stress-optical material 19, a light source 23 and a camera 8 in a separate, enclosed unit 24 (see FIG. 4a). Said unit 24 is mounted on the towed implement 4 (or also on the lower link of the lifting mechanism 14 of the agricultural tractor) in such a way that the stress-optical material 19 is fastened directly to the carrier material and can therefore detect the stresses. The transmission of energy and data to the vehicle 2 (if it is not installed on the lower link of the lifting mechanism 14) is carried out e.g. by means of cables into which the data lines are integrated. In addition, optical stress sensors can be mounted either on the lower link 17 or on the carrier 22 of the plow in order therefore to infer the tensile force during plowing.

In addition, by way of example a method for operating the vehicle 2 with a hydraulic activation unit for controlling the operation of a towed implement 4 is illustrated here. Firstly, the state of the stress-optical material 19 is detected by means of the camera 8 which is directed towards it. The (current) tensile force of the towed implement 4 is then determined from the detected state of the stress-optical material 19. The tensile force (load on the towed implement 4) which is determined in this way is then compared with a (stored or desired) tensile force. If the determined tensile force differs from the reference tensile force (more than desired or permitted), the hydraulic activation unit or the lifting mechanism 15 is activated and the towed implement 4 is pivoted. The driving speed of the vehicle 2 can also be adapted alternatively or cumulatively.

LIST OF REFERENCE NUMBERS

1 Device
2 Vehicle
3 Hydraulic activation unit
4 Towed implement
5 Ground
6 Driving direction
7 Position detection unit
8 Camera
9a First position detection mark
9b Second position detection mark 9c Third position detection mark
10 Evaluation unit
11 Data-transmitting connection
12 Vehicle controller
13 Control unit
14 Lifting mechanism
15 Lifting mechanism
16 Upper link
17 Lower link
18 Tensile force-measuring apparatus
19 Stress-optical material
20 Pump
21 Control valve
22 Carrier
23 Light source
24 Unit
25 Vertical position
26 Reference vertical position

What is claimed is:

1. A device for a vehicle having a hydraulic activation unit configured to control an operation of a towed implement of the vehicle, the device comprising:
  at least one position detection unit having at least one camera;
  at least one position detection mark arranged on one of (i) the towed implement and (ii) the hydraulic activation unit configured to control an operation of the towed implement, wherein the at least one camera is directed toward the at least one position detection mark to generate image data indicative of the position of the at least one position detection mark;
  an evaluation unit connected to said at least one camera and configured and adapted to (i) determine a position of the towed implement from the image data, (ii) compare the position to a reference position, and (iii) activate the hydraulic activation unit to adjust the position of the towed implement in response to a difference in the position and the reference position; and
  a data-transmitting connection from the evaluation unit to a control unit that is assigned to the hydraulic activation unit.

2. The device according to claim 1, wherein the at least one camera is arranged on one of (i) the vehicle and (ii) the towed implement.

3. The device according to claim 1, wherein the at least one position detection mark includes a plurality of position detection marks that are spaced apart from one another.

4. The device according to claim 1, further comprising:
  a tensile force-measuring apparatus connected to the evaluation unit in a data-transmitting fashion.

5. The device according to claim 4, wherein:
  the tensile force-measuring apparatus is coupled to the at least one camera; and
  the at least one camera is directed toward a stress-optical material arranged on one of (i) the towed implement and (ii) the hydraulic activation unit configured to control the towed implement.

6. The device according to claim 5, wherein the stress-optical material is attached to one of (i) the towed implement and (ii) a lifting mechanism of the towed implement.

* * * * *